United States Patent [19]  [11] 3,931,159
Wei et al.  [45] Jan. 6, 1976

[54] SUBSTITUTED 3-BENZOYLACRYLAMIDO-CEPHALOSPORANIC ACID DERIVATIVE

[75] Inventors: Peter H. L. Wei, Springfield; Ronald J. McCaully, Malvern, both of Pa.

[73] Assignee: American Home Products Corporation, New York, N.Y.

[22] Filed: Mar. 18, 1974

[21] Appl. No.: 452,013

[52] U.S. Cl............ 260/240 J; 260/243 C; 424/246
[51] Int. Cl.[2]............... C07D 501/22; C07D 501/24
[58] Field of Search .................... 260/240 J, 243 C

[56] References Cited
UNITED STATES PATENTS
3,338,896  8/1967  Takano et al. ................ 260/243 C
3,546,219  12/1970  Long et al. .................... 260/243 C FOREIGN PATENTS OR APPLICATIONS
1,058,535  2/1967  United Kingdom ............ 260/243 C Primary Examiner—Arthur P. Demers
Attorney, Agent, or Firm—Richard K. Jackson

[57] ABSTRACT

The invention provides anti-bacterial agents of the formula:

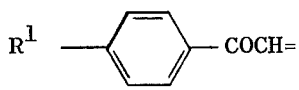

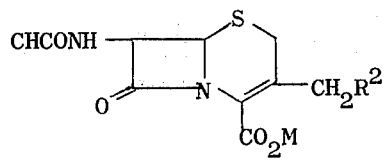

$R^1$ is a member selected from the group consisting of —Cl and

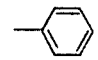

$R^2$ is a member selected from the group consisting of —H and acetoxy; and
M is a member selected from the group consisting of —H, an alkali metal and —$NH_4$.

2 Claims, No Drawings

SUBSTITUTED 3-BENZOYLACRYLAMIDO-CEPHALOSPORANIC ACID DERIVATIVE

BACKGROUND OF THE INVENTION

Certain α, β-unsaturated amides of 7-aminocephalosporanic acid are disclosed in Japanese Patent No. 16,950/66 (Sept. 26, 1966) as abstracted in Derwent 23,236.

DESCRIPTION OF THE INVENTION

In accordance with this invention there is provided a group of anti-bacterial agents of the formula:

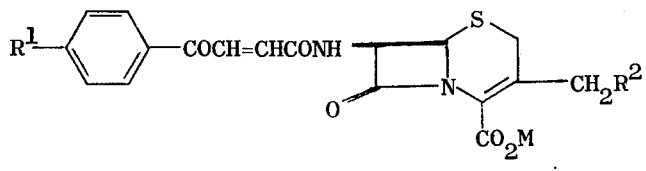

in which
R[1] is a member selected from the group consisting of —Cl and

R[2] is a member selected from the group consisting of —H and acetoxy; and
M is a member selected from the group consisting of —H, and alkali metal and —$NH_4$.

The compounds of this invention are prepared by known techniques, in that the 3-(p-substituted benzoyl) acrylic acid is coupled with the 7-amino-cephalosporanic acid derivatives by the mixed anhydride method commonly employed in the formation of amide linkages in polypeptide chemistry.

The compounds of this invention were proven to be effective anti-bacterial agents against gram-positive, gram-negative and resistant strains of bacteria, by testing them in the well known and scientifically accepted agar serial dilution testing technique. Thus, the compounds of this invention are useful in the fields of comparative pharmacology and in microbiology and for the treatment of bacterial infections amenable to treatment with cephalosporin antibiotics.

The following examples illustrate the preparation of representative cephalosporin derivatives within the ambit of the generic aspect of the invention. The activity of each product is presented for those specific bacterial strains against which the compound exemplified was active in providing 100 percent growth inhibition at or below 250 micrograms per milliliter. The representative nature of the bacterial strains employed to demonstrate antibacterial activity are indicative of the broader applicability of the compounds of this invention in the control of bacterial infestations other than those specifically referred to in each of the following examples. The bacteria are named, followed by the specific strain and the concentration in micrograms per milliliter at which 100 percent inhibition occurred. The abbreviations for each bacterium are:

| | |
|---|---|
| BA SU | Bacillus subtilis |
| HE SP | Herellea species |
| NE CA | Neisseria catarrhalis |
| ST AU | Staphylococcus aureus |

EXAMPLE I

7-[3-(p-Chlorobenzoyl)acrylamido]cephalosporanic acid

To a tetrahydrofuran solution of 1.08 grams (5 millimole) of 3-(p-chlorobenzoyl) acrylic acid in a salt-ice bath was added triethylamine (0.50 gram), followed by 0.70 gram (5 millimole) of isobutyl chloroformate. After the solution was stirred for 15 minutes a cold solution of 1.36 grams (5 millimole) 7-amino-cephalosporanic acid and 0.50 gram of triethylamine in 20 milliliters tetrahydrofuran and 10 milliliters $H_2O$ was slowly added. The mixture was stirred in the ice bath for 1 hour and at room temperature for 1 hour. After filtration of a solid the filtrate was evaporated under reduced pressure at approximatly 30°C. The residue was partly dissolved in 50 milliliters $H_2O$ and filtered. The aqueous filtrate was acidified with a 6N HCl solution. The resultant precipitate was collected and washed well with $H_2O$. The solid was dissolved in ethyl acetate, and the solution dried over anhydrous $MgSO_4$. After the solvent was removed the residual solid was treated with pentane and collected to give 1.5 grams of the title compound.

Elemental Analysis for $C_{20}H_{17}ClN_2O_7S$: Calc'd: C, 51.68; H, 3.69; N, 6.03. Found: C, 52.15; H, 4.01; N, 5.65.

| | | |
|---|---|---|
| BA SU | 6633 | 1.95 |
| HE SP | 9955 | 250 |
| ST AU | 6538P | 1.95 |
| ST AU | SMITH | 1.95 |
| ST AU | CHP | 7.81 |
| ST AU | 53–180 | 15.6 |

EXAMPLE II

7-[3-(p-Chlorobenzoyl)acrylamido]-3-methyl-8-oxo-5-thia-1-azabicyclo[4.2.0]oct-2-ene-2-carboxylic acid The title compound was prepared by the procedure described in Example 1 except that 7-amino desacetoxycephalosporanic acid was substituted for 7-aminocephalosporanic acid.

Elemental Analysis for $C_{18}H_{17}ClN_2O_5S$: Calc'd: C, 53.13; H, 3.82; N, 6.89. Found: C, 53.07; H, 3.99; N, 6.68.

| | | |
|---|---|---|
| BA SU | 6633 | 31.3 |
| HE SP | 9955 | 250 |
| ST AU | 6538P | 7.81 |
| ST AU | SMITH | 7.81 |
| ST AU | CHP | 31.3 |
| ST AU | 53–180 | 31.3 |

EXAMPLE III

7-[3-(4-Biphenylylcarbonyl)acrylamido]cephalosporanic acid

The title compound was prepared by the procedure described in Example 1, except that 3-(4-biphenylylcarbonyl)acrylic acid was substituted for 3-(p-chlorobenzoyl) acrylic acid.

Elemental Analysis for $C_{26}H_{22}N_2O_7S$: Calc'd: C, 61.68; H, 4.38; N, 5.53. Found: C, 61.97; H, 4.58; N, 5.30.

| | | |
|---|---|---|
| HE SP | 9955 | 250 |
| ST AU | 6538P | .976 |
| ST AU | SMITH | .976 |
| ST AU | CHP | 1.95 |
| ST AU | 53–180 | 1.95 |
| BA SU | 6633 | 3.90 |

What is claimed is:
1. The compound which is 7-[3-(p-chlorobenzoyl)acrylamido]-3-methyl-8-oxo-5-thia-1-azabicyclo[4.2.0]oct-2-ene-2-carboxylic acid.
2. The compound which is 7-[3-(4-biphenylyl-carbonyl)acrylamido]cephalosporanic acid.

* * * * *